(12) United States Patent
Lootz

(10) Patent No.: US 6,613,080 B1
(45) Date of Patent: Sep. 2, 2003

(54) STENT WITH CLOSED STRUCTURE

(75) Inventor: Daniel Lootz, Rostock (DE)

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/695,722

(22) Filed: Oct. 24, 2000

(30) Foreign Application Priority Data

Oct. 26, 1999 (DE) .......................................... 199 51 611

(51) Int. Cl.⁷ ................................................. A61F 2/06
(52) U.S. Cl. ....................................................... 623/1.15
(58) Field of Search ............................... 623/1.15, 1.18, 623/1.17, 1.12, 1.16, 1.2; 606/191, 198, 108, 194

(56) References Cited

U.S. PATENT DOCUMENTS

| | | | |
|---|---|---|---|
| 4,655,771 A | 4/1987 | Wallsten | |
| 5,104,404 A | 4/1992 | Wolff | |
| 5,755,776 A | * 5/1998 | Al-Saadon | 623/1.15 |
| 5,776,183 A | * 7/1998 | Kanesaka et al. | 623/1.15 |
| 5,843,164 A | 12/1998 | Frantzen | |
| 5,843,175 A | * 12/1998 | Frantzen | 623/1.15 |
| 6,027,527 A | * 2/2000 | Asano et al. | 623/1.15 |
| 6,117,165 A | * 9/2000 | Becker | 606/191 |
| 6,132,461 A | * 10/2000 | Thompson | 623/1.15 |
| 6,197,047 B1 | 3/2001 | Kranz | |
| 6,241,762 B1 | * 6/2001 | Shanley | 623/1.17 |
| 6,251,134 B1 | 6/2001 | Alt et al. | |
| 6,309,414 B1 | * 10/2001 | Rolando et al. | 623/1.15 |
| 6,395,020 B1 | * 5/2002 | Ley et al. | 623/1.15 |

FOREIGN PATENT DOCUMENTS

| | | |
|---|---|---|
| DE | 197 22 857 A1 | 11/1998 |
| DE | 199 50 756 A1 | 8/2000 |
| EP | 0 540 290 A2 | 5/1993 |
| WO | WO 98/44872 A1 | 4/1998 |

* cited by examiner

*Primary Examiner*—A. Vanatta
(74) *Attorney, Agent, or Firm*—Hahn Loeser + Parks LLP; Stephen L. Grant

(57) ABSTRACT

The invention concerns a stent, in particular a coronary stent, comprising a tubular portion, wherein openings are provided in the tubular portion. The invention is distinguished in that the openings provided in the tubular portion of the stent are of a substantially T-shaped configuration.

18 Claims, 1 Drawing Sheet

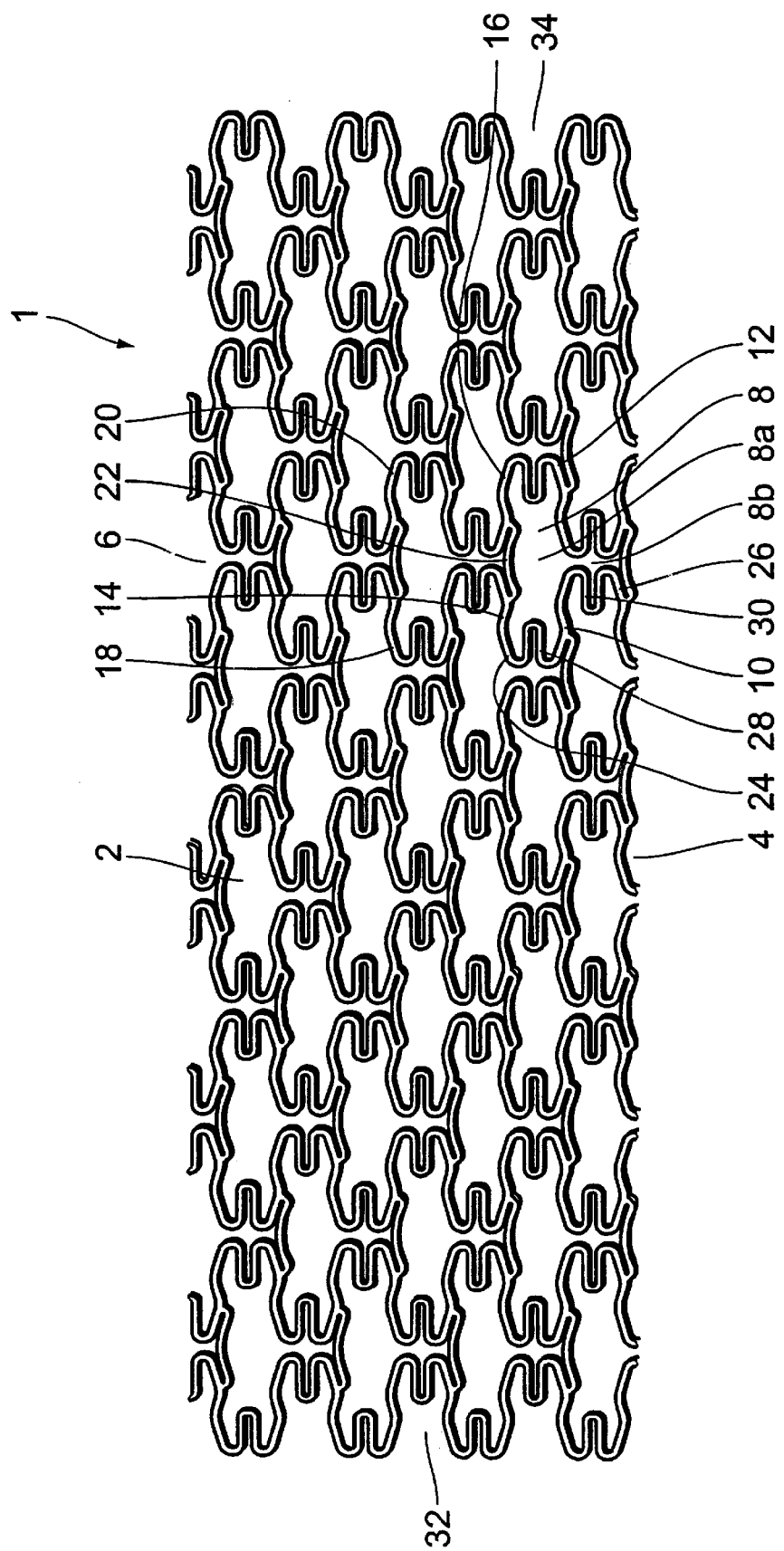

STENT WITH CLOSED STRUCTURE

The invention concerns a stent having a tubular portion which has openings.

BACKGROUND OF THE ART

Stents of that kind are known from the state of the art in many different forms. Those stents are used inter alia in connection with percutaneous transluminal angioplasty (PCTA, Percutaneous Transluminal Balloon Angioplasty), in vascular surgery of the heart. Stents however can also serve to dilate other openings in the body or to keep such openings in a dilated condition. That medical procedure is initially preceded by determining the location of the constriction in a coronary blood vessel. A so-called angioplasty balloon is then moved in the artery which has the constriction, the so-called stenosis, to the location of the stenosis where it is inflated. Due to the radially outwardly directed force of the inflated balloon the constriction is dilated and in the optimum case the original passage cross-section of the previously constricted artery is restored. Besides successful dilation of the vessel however side-effects can also occur, which include local splits in the artery, disintegration effects and projections of plate portions and flakes into the lumen of the artery so that, in spite of the dilation effect, blockage of the vessel can still occur. In addition it is possible that a stenosis can recur due to the vessel wall elastically springing back and/or due to the growth of the intima of the vessel. Statistically, that occurs within six months in the case of over 30% of the patients who were treated with PCTA.

In order now immediately after dilation of the vessel to ensure a relatively smooth inside wall surface for the vessel and to be able to avoid renewed stenosis, the stents set forth in the opening part of this specification were developed. Those small tubes serve inter alia in conjunction with PCTA to maintain the vessel flow cross-section which is produced by balloon angioplasty in order thereby to ensure long-term success with the PCTA procedure.

The success of such so-called stenting also depends inter alia on how uniformly the stent can come to bear against the wall of the vessel. For, the more uniformly the wall of the vessel is supported, the correspondingly more probable it is that vessel constrictions will not recur in the region of the stent. In that respect a regular stent structure produces a relatively smooth inside surface for the vessel and, with a relatively smooth inside vessel surface, blood particles can only be deposited thereon with difficulty. In addition growths of the intima into the interior of the vessel are prevented to a greater degree by a regular stent structure which covers over the inside surface of the vessel in a relatively closed configuration.

Stents of that kind with a so-called closed structure are also known from the state of the art. By way of example reference may be made here to one of the best-known stents of that kind, the so-called wall stent. That is known for example from U.S. Pat. No. 4,655,771. This stent which has a closed structure is formed from a plurality of wires which are regularly knitted in a mesh-like structure and which extend in a spiral configuration on the longitudinal axis of the stent.

The advantage of the closed structure of stents of that kind is however only achieved at the cost of the disadvantage that the stents involve relative longitudinal stiffness during insertion. Those stents do not therefore make it possible in the optimum manner for the stent to be guided through possibly very severely curved vessel portions in the coronary arteries upon insertion in a direction towards the stenosis to be treated. In order to avoid those disadvantages of a closed structure, stents have now been developed which are of a so-called modular nature. In the case of those stents of a modular nature, individual portions which are provided with a closed structure are connected together by flexible connections. Stents of that kind are known for example from U.S. Pat. No. 5,104,404.

A disadvantage with those modular or segmented stents however is that the front edges of each individual module or segment, which lead in the direction of insertion of the stent, can hook in the inside wall of the vessel. That can give rise to serious complications when inserting a stent. That is particularly problematical more especially insofar as the modular stents—as already referred to above—are used in particular when major curvatures have to be negotiated on the way to the location to be treated. For, it is in such a curve that such a leading edge of a segment becomes particularly easily hooked at the inside surface of the vessel, which is on the outside of the curvature, through which the stent is being passed.

Therefore the object of the invention is to avoid the above-mentioned disadvantages and to provide a stent of the kind set forth in the opening part of this specification which both permits the inside surface of the vessel to be covered in a closed configuration at the location of the stenosis to be treated while at the same time it is sufficiently flexible that it can be displaced to that location.

SUMMARY OF THE INVENTION

In the case of the present invention that object is attained by a stent of the kind set forth in the opening part of this specification, in that the openings provided in the stent are of a substantially T-shaped configuration.

The advantages of the invention are in particular that the T-shaped openings in the tubular structure of the stent provide a structure which is closed overall so as to provide for good covering of the lesion while at the same time by virtue of the T-shaped openings the flexibility in the longitudinal direction of the stent is increased in comparison with the closed stent structures which are known from the state of the art.

The invention involves the realization that the openings which are of a T-shaped configuration in accordance with the invention mean that those openings have two portions which extend substantially perpendicularly to each other. These involve on the one hand the portion of the opening, which forms the crossbar of the T-shape, and the portion of the opening, which forms the upright leg of the T-shape. In this case the crossbar of the T-shape preferably extends in the longitudinal direction of the tubular portion of the stent while the upright leg of the T-shape preferably extends in the peripheral direction of the tubular portion of the stent according to the invention. That configuration ensures that the stent has flexibility in both of the above-mentioned directions, such flexibility imparting to the stent according to the invention overall a degree of flexibility as is required for example when pushing the stent through curves in coronary blood vessels.

In a preferred configuration of the present invention the tubular portion has a peripheral surface, wherein the openings in the tubular portion are defined by bars, which bars are formed from the remaining material of a tube wall, forming the peripheral surface, of the tubular portion, the material having been removed from that tube wall in the region of the openings. This embodiment is distinguished in that the bars define the openings in the direction of the longitudinal axis of the tubular portion, substantially in the form of an S. This embodiment is advantageously distinguished in that an enhanced degree of flexibility of the stent is achieved by virtue of the S-shaped bars defining the openings, as the S-shape is inherently flexible. In addition, with this embodiment it is preferred if the S-shaped bars are arranged in such a way that the respective S-shape formed is disposed in the peripheral direction. For, in that way it is possible for the respective curve or bulge portions of the S-shape, upon insertion of the stent into curved coronary blood vessels, to be pushed into the adjacent bend configuration or the adjacent bulge portion of the same S-shape or the peripherally adjacent S-shape of the bars in order in that way to guarantee stent flexibility. A further advantage of this embodiment is that when crimping of the stent is effected a smaller crimp profile is produced. With this embodiment, that smaller crimp profile is made possible by the S-shaped bars without the bars touching each other. The smaller diameter of the crimp profile which can be achieved in that way facilitates access to stenoses and makes it easier to reach remote stenoses by means of such a stent.

In a further preferred embodiment of the invention the openings are of a mirror image-symmetrical configuration with respect to a peripheral line intersecting them. That configuration ensures that, upon being dilated, the stent expands uniformly without the stent structure suffering from being pulled askew upon expansion.

A further development of the invention is distinguished in that the bars define the openings in such a way that the parts of the T-shaped openings, which form the upright legs of the T-shape, extend substantially in the peripheral direction of the tubular portions. In that case, it is further preferred if the bars define the openings in such a way that the parts of the openings, which form the crossbars of the T-shaped openings, extend substantially in the longitudinal direction of the tubular portions of the stent. That regular arrangement of the bars provides for an optimally closed structure with its advantages as set forth in the opening part of this specification. At the same time however the openings which are of a T-shaped configuration in that way provide that the parts of the openings, which form the crossbar of the T-shape, are laterally movable in the optimum fashion, as is a considerable advantage for example when introducing the stent into severe curvatures in coronary blood vessels.

In a further preferred embodiment of the present invention the portions of the bars which form the ends of the S-shaped bars defining the openings in the longitudinal direction of the tubular portion are respectively connected by way of connecting means to the portions which form the corresponding ends and which are disposed in opposite relationship in mirror image-symmetry with respect to the T-shaped opening enclosed by the bars. In that respect it is preferred if the connecting means are bars extending substantially in the longitudinal direction of the tubular portion of the stent according to the invention. Those bars can further preferably be of a slightly curved configuration in a lateral direction in order to enhance the flexibility of the stent also in that region of the connecting means. Overall however this configuration according to the invention makes it possible to achieve optimum application to the overall structure of the stent, of the various forces which occur upon flexural movements of the tubular portion.

In a further preferred embodiment of the present invention the S-shaped bars are of an inwardly inverted configuration at at least one of the bulge portions of the S-shape. Those inwardly inverted portions which in a further preferred feature are inverted inwardly into the bulge configuration of the corresponding S-shape by at least 50% of said bulge configuration, make it possible in a particularly advantageous fashion to successfully avoid an axial reduction in the length of the stent upon radial expansion thereof. For, those inwardly inverted portions which are incorporated into the bulge-shaped regions of the S-shaped bars afford a radial expansion potential for the stent, without that being at the expense of the length of the stent. In addition those inwardly inverted portions also provide for a further increase in the flexibility of the stent as those curve portions further increase the lateral mobility of the S-shaped bars.

These structures, which are also to be referred to as a double curve, consisting of S-shaped bars and inwardly inverted portions in the bulge portions of the S-shaped bars, therefore serve in a quite particular fashion to attain the object of the invention.

In a further development of the stent according to the invention the part of the opening, which forms the crossbar of the T-shape, is wider than the part forming the upright leg of the T-shape. By means of this embodiment it is advantageously possible for the stent also to be fitted in the region of vessel branchings in a procedure for stenting coronary blood vessels. With this embodiment it is an easy matter to incorporate windows into a design of this kind. For, by virtue of the closed, homogenous and regular structure, such a windowing configuration for a given region of the tubular portion of the stent according to the invention does not have a detrimental effect on the strength of the overall structure. That is also afforded inter alia by the interleaving relationship of the T-shaped openings. For, that interleaving configuration in turn provides that the peripheral surface of the stent is in particular uniformly covered in the expanded condition so that, when the stent is in the expanded condition, no relatively large interconnected free areas remain open in the peripheral surface. Accordingly the closed homogenous stent structure according to the invention is not only found to be more flexible in comparison with the known state of the art in respect of closed structures of that kind; on the contrary, by means of that structure, it is also readily possible to provide windows for a vessel branching in the stent. For, window configurations of that kind are not readily possible in the state of the art with the previously known closed structures as they are excessively tightly structured, that is to say they do not afford adequate options in terms of providing and incorporating a window of that kind.

A further advantage of the interleafing arrangement as already referred to above becomes clear when considering the cross-section of the expanded stent, that is to say when considering it in the axial direction. For, the deformable T-shaped elements of the stent according to the invention are further divided by the above-mentioned inwardly inverted portions extending into the bulge configurations of the S-shaped bars. The consequence of this is that the stent is constructed generally and in particular in the peripheral direction from comparatively short bars. Therefore the bars defining the T-shaped openings have only relatively short straight bar portions. As however upon expansion of the stent the deformation of the bars occurs in particular in the region of the radii, that is to say the curves in the bars, the stent according to the invention involves an approximation of the expanded stent cross-section to a circular shape in a particular fashion. That improves the adaptability of the stent according to the invention to the surrounding vessel, in comparison with the stent known from the state of the art.

For, the known stents to be found in the state of the art have only relatively long bar segments which only insufficiently approach a circular shape upon expansion of the stent in respect of the stent cross-section. In the state of the art therefore there is the disadvantage that individual bar portions, in the expanded stent, project into the interior of the vessel and thus disadvantageously impede the free flow of blood therethrough.

A particularly preferred embodiment of the invention is distinguished in that all openings are of the same size. The stent is accordingly preferably constructed from regularly repeating, always identical structural elements or so-called unit cells.

Further preferred embodiments of the invention are set forth in the appendant claims.

BRIEF DESCRIPTION OF THE DRAWINGS

An embodiment by way of example of the present invention will now be described with reference to the single FIGURE.

DETAILED DESCRIPTION OF THE INVENTION

The FIGURE shows a stent 1 according to the invention. The stent 1 is shown in the FIGURE as a development of the peripheral surface 2 of the stent 1. When the stent 1 is in the condition of being ready for operation, the peripheral surface 2 is joined together with its side 4 which is shown at the bottom in the FIGURE and the side 6 which is shown at the top in the FIGURE, so as to afford a tubular portion having the peripheral surface 2.

The peripheral surface 2 has first T-shaped openings 8. All T-shaped openings are of an identical shape and are of the same size. The T-shaped openings 8 are arranged in mutually interleaved relationship on the peripheral surface. The T-shaped openings have a wide upper part 8a which is shown in each case at the top in the FIGURE and which forms the crossbar of the T-shape, and a lower part 8b which is shown at the bottom in the FIGURE and which forms the upright leg of the T-shape. The upper part 8a and the lower part 8b thus form the T-shaped openings 8.

The T-shaped openings 8 are each defined in the FIGURE on the left-hand side by an S-shaped bar 10. Arranged in mirror image-symmetrical relationship with the respective S-shaped bar 10, in relation to a peripheral line which centrally intersects the respective one of the openings 8 and which in the FIGURE respectively extends downwardly, is a bar 12 which is of an S-shaped configuration in mirror-inverted relationship.

At the upper ends 14 and 16 of the bars 10 and 12 respectively, they are connected, as viewed in the peripheral direction of the peripheral surface 2, to respective identical bars 18 and 20. Together the S-shaped bars 10 and 18, 12 and 20 respectively form rectangular curves extending in the peripheral direction.

In addition the bars 10 and 12 respectively which hereinbefore and also hereinafter are picked out only by way of example from the overall structure in the FIGURE are also connected together with their ends 14 and 16 respectively by way of a connecting bar 22 which serves as a connecting means in accordance with the invention and which in the FIGURE is of a slightly upwardly arcuate configuration. In this arrangement the connecting bar 22 extends substantially in the longitudinal direction of the stent 1. Each of the ends of the illustrated bars 10 and 12 respectively, which correspond to the ends 14 and 16 which have been picked out by way of example, are connected together by way of connecting bars 22 of that kind. All the connecting bars 22 are also exactly identical. The connecting bars 22 engage points, which are neutral in respect of length, of the ends 14 and 16 of the bars 10 and 12 respectively. That minimizes the axial reduction in length of the stent 1 upon expansion thereof.

The surface area extent of the part 8a forming the crossbar of the T-shaped openings 8 is between approximately four and five times as great as that of the part 8b forming the upright leg of the openings 8. In particular the width of those parts of the openings, as measured in the lengthwise extent of the respective parts 8a and 8b, is different, so that the width of the part 8a forming the crossbar is between approximately twice and three times as great as the width of the part 8b of the opening 8, which forms the upright leg.

In addition the S-shaped bars 10 and 12 defining the T-shaped openings 8 have the outward loop or bulge portions 24 and 26 which in themselves produce the S-shape of the bars. Provided in those bulge portions 24 and 26 which form the actual S-shape of the bars 10 and 12 respectively are inwardly inverted portions 28 and 30 which extend in opposite relationship to the direction in which the bulge portions extend. Those inwardly inverted portions 28 and 30 project as substantially U-shaped salients into the opening 8 in the region of the upper parts or crossbars 8a while they increase the width of the opening 8 in the region of the lower parts 8b. By virtue of the interleaved structure however the increased-width portions of the lower parts 8b simultaneously represent the constrictions in the region of the upper parts 8a.

By virtue of the S-shaped boundaries of the openings 8 the entire peripheral surface of the stent structure can also be of a closed configuration at the edges 32 (at the left in the FIGURE) and 34 (at the right in the FIGURE), so that there are no pointed ends which could possibly hook into openings in the body in the procedure for introducing the stent.

What is claimed is:

1. A stent, having a longitudinal and a peripheral direction, comprising;
   a tubular portion having a plurality of substantially T-shaped openings, arranged in adjacent mutually interleaved relationship, each said T-shaped opening having an upright leg and a crossbar;
   the T-shaped openings being defined by a plurality of bars, such that a portion of each bar that defines the upright leg of each of the T-shaped openings comprises a substantially U-shaped salient that extends into the crossbar of one of the adjacent T-shaped openings.

2. The stent as set forth in claim 1 wherein each of the openings is of a mirror image-symmetrical configuration with respect to a line extending through the openings in the peripheral direction.

3. The stent of claim 1 wherein the tubular portion has a peripheral surface, wherein said bars which define the openings are formed from the remaining material of a tubular wall, forming the peripheral surface, of the tubular portion, from which tubular wall the material was removed in the region of the openings, and wherein the bars have end portions and a substantially S-shape in the peripheral direction of the tubular portion.

4. The stent as set forth in claim 3 wherein the bars are arranged such that the upright legs of the T-shaped openings extend substantially in the peripheral direction of the tubular portion.

5. The stent of claim 4 wherein the bars are arranged such that the crossbars of the T-shaped openings extend substantially in the longitudinal direction of the tubular portions.

6. The stent of claim 5 wherein the end portions which form the ends of the S-shaped bars defining the openings in the longitudinal direction are respectively connected through a means for connecting to the end portions which form the corresponding ends and which are disposed in opposite, mirror image-symmetrical relationship with respect to the T-shaped opening.

7. The stent as set forth in claim 6 wherein the connecting means are bars extending substantially in the longitudinal direction of the tubular portion.

8. The stent of claim 1 wherein the crossbar of the T-shape is wider than the upright leg of the T-shape.

9. The stent of claim 1 wherein all said openings are of equal size.

10. The stent of claim 2 wherein the tubular portion has a peripheral surface, wherein said bars which define the openings are formed from the remaining material of a tubular wall, forming the peripheral surface of the tubular portion, from which tubular wall the material was removed in the region of the openings, and wherein the bars have end portions and a substantially S-shape in the peripheral direction of the tubular portion.

11. The stent as set forth in claim 10 wherein the bars are arranged such that the upright legs of the T-shaped openings extend substantially in the peripheral direction of the tubular portion.

12. The stent of claim 11 wherein the bars are arranged such that the crossbars of the T-shaped openings extend substantially in the longitudinal direction of the tubular portions.

13. The stent of claim 12, wherein the end portions which form the ends of the S-shaped bars defining the openings in the longitudinal direction are respectively connected through a means for connecting to the end portions which form the corresponding ends and which are disposed in opposite, mirror-image symmetrical relationship with respect to the T-shaped opening.

14. The stent as set forth in claim 13 wherein the connecting means are bars extending substantially in the longitudinal direction of the tubular portion.

15. The stent of claim 3 wherein each said S-shaped bar comprises an inwardly inverted portion and an outward bulge portion to define the S-shape.

16. The stent of claim 15 wherein each inwardly inverted portion is configured in opposite longitudinal relationship to the corresponding bulge portion of the S-shaped bar.

17. The stent of claim 14 wherein each said S-shaped bar comprises an inwardly inverted portion and an outward bulge portion to define the S-shape.

18. The stent of claim 17 wherein each inwardly inverted portion is configured in opposite longitudinal relationship to the corresponding bulge portion of the S-shaped bar.

* * * * *